US005635193A

United States Patent [19]
Walter et al.

[11] Patent Number: 5,635,193
[45] Date of Patent: Jun. 3, 1997

[54] STABILITY OF AZADIRACHTIN-CONTAINING SOLID

[75] Inventors: James F. Walter, Ashton; Michael T. Roland, Eldersburg, both of Md.

[73] Assignee: Thermo Trilogy Corporation, Waltham, Mass.

[21] Appl. No.: 482,048

[22] Filed: Jun. 7, 1995

[51] Int. Cl.$^6$ .................................................. A01N 65/00
[52] U.S. Cl. ............... 424/405; 424/195.1; 424/DIG. 10; 514/453; 514/919
[58] Field of Search ..................... 424/405, 195.1, 424/DIG. 10; 514/453, 919

[56] References Cited

U.S. PATENT DOCUMENTS

| | | | |
|---|---|---|---|
| 4,556,562 | 12/1985 | Larson | 424/195.1 |
| 4,946,681 | 8/1990 | Walter | 424/195.1 |
| 5,001,146 | 3/1991 | Carter et al. | 514/453 |
| 5,397,571 | 3/1995 | Roland et al. | 424/405 |

*Primary Examiner*—John W. Rollins
*Attorney, Agent, or Firm*—Quarles & Brady

[57] ABSTRACT

The stability of an azadirachtin-containing solid preparation is increased if the preparation contains about 5% or less volatile polar solvents and 1% or less water. Reduction of the percentage of volatile polar solvents present in preparations of azadirachtin-containing solids to such levels improves the storage-stability of the solids without significantly degrading the azadirachtin in the solid. Solvents are preferably removed by drying the preparation at a suitable temperature for a time sufficient to reduce the level of water and volatile polar solvents to acceptable levels.

11 Claims, No Drawings

STABILITY OF AZADIRACHTIN-CONTAINING SOLID

FIELD OF THE INVENTION

This invention relates to pesticide compositions and more particularly to an azadirachtin-containing biocontrol agent in solid form that is characterized by improved stability.

BACKGROUND OF THE INVENTION

The biological activities of the neem tree seeds have long been recognized. Of primary importance are the potent insecticidal and pesticidal properties of azadirachtin, the main active ingredient in the neem seed. Azadirachtin is a tetranortriterpenoid that causes feeding inhibition and growth disruption in various insect, mite, nematode, etc. orders.

There are various methods known to extract azadirachtin from neem seeds. Typically, these methods involve drying the neem seeds, milling the dried seeds to a coarse powder, and extracting the powder with various solvents such as methanol, ethanol, water, methylene chloride, chloroform, hexane methylethylketone, butanol, petroleum benzene, ether, acetone, methyl tertbutyl ether, diethylcarbonate, etc. In general, it has been found that the efficiency of the extract yield can be increased by increasing the solvent polarity, i.e., from hexane to ethanol, ethanol to methanol, etc. However, despite the initial drying of the neem seeds, they still may contain between 6 to 15% water. Thus, while the utilization of more polar solvents will increase the extraction efficiency relative to azadirachtin, it will also extract more of the water contained within the neem seeds and results in aqueous-containing extracts. That is, since water and azadirachtin have similar solubilities, the solvents useful for extracting the azadirachtin from neem seeds also extract water contained therein. Crude neem seed extracts may contain up to 20% water.

Early study of the bioactive properties of neem seeds was directed to identifying fractions, including oil and wax fractions that retained bioactivity after preparation. See, e.g., Singh, et al., *Phytoparasitica*, 16:3, 1988. U.S. Pat. No. 4,556,562 (Larson) teaches a storage-stable, acidified aqueous ethanol extract of azadirachtin prepared from ground neem seeds. An accepted method for preparing azadirachtin includes extracting oil from the seeds with an azadirachtin-insoluble solvent such as hexane, followed by a second extraction using an azadirachtin-soluble solvent such as ethanol to obtain an azadirachtin-containing extract solution. However, U.S. Pat. No. 4,946,681 (Walter) teaches that protic solvents having acidic or basic functional groups decrease the storage stability of azadirachtin. U.S. Pat. No. 4,946,681 teaches a method for using molecular sieves to remove water from an extract solution without removing azadirachtin, to improve the storage stability of the extract. The same patent also teaches that the storage stability of azadirachtin in an extract solution varies greatly, depending upon the solvent system of the extract. Storage stability is enhanced when the extract solution comprises greater than 50% by volume aprotic solvents and less than 15% water. Aprotic solvents are defined in U.S. Pat. No. 4,946,681 as polar solvents having moderately high dielectric constants which do not contain acidic hydrogen, including, but not limited to, aliphatic alcohols, ketones, nitriles, substituted aromatics, amide sulfoxides, alkyl carbonates, chlorinated aliphatics, aromatic aldehydes, sulfones, ethers, esters, and the like, or mixtures thereof. U.S. Pat. No. 5,001,146 (Carter, et al.) teaches storage of azadirachtin in non-degrading solvent systems that offer improved shelf-life stability over ethanol-water based formulations. U.S. Pat. No. 5,001,146 also teaches that if the protic solvent is an alcohol, the concentration of water must be less than 5% water by volume, and is preferably less than 2%, and most preferably less than 1% of the total solution.

At present, all commercial preparations comprising azadirachtin are organic solutions. The commercial use of azadirachtin has been limited as a result of storage instability of the compound. Water has been identified as the primary cause of degradation of azadirachtin in solution.

Several methods are known for preparing solid azadirachtin. U.S. Pat. No. 5,397,571 (Roland, et al.) describes a method for co-extracting azadirachtin and neem oil from ground neem seeds. One product of the method of U.S. Pat. No. 5,397,571 is an azadirachtin-containing solid having greater than 10 weight percent of azadirachtin. Briefly, in this method, ground neem seeds are co-extracted with a mixture of nonpolar, aliphatic hydrocarbon solvents and polar solvents, each present in an amount sufficient to permit extraction of both the hydrophilic and hydrophobic components desired from the neem seeds. The hydrophilic and hydrophobic portions of the solvent extract mixture are separated from each other, preferably using a counter-extraction process, whereby the solvent is removed from the solvent extract mixture to leave a neem extract mixture that contains both the hydrophilic and the hydrophobic portions. The neem extract mixture is then contacted with a solvent having a sufficiently low polarity (i.e., hexane) to precipitate as a solid the hydrophilic, azadirachtin-containing portion of the extract. The solid is then recovered by a known technique, such as filtration.

In the method of Schroeder, D. R. and K. Nakanishi, *J. Natural Products* 50:241–244 (1987), neem seeds are exhaustively defatted with hexane and are then extracted with 95% ethanol/5% water. The ethanol extract is then partitioned between petroleum ether and 95% aqueous methanol. The ether phase, containing oils and non-polar materials, is discarded. The methanol phase is then partitioned between water and ethyl acetate. The water phase is discarded and the acetate phase is vacuum-filtered through a plug of Si gel and then concentrated. The concentrated filtrate is subjected to vacuum liquid chromatography in hexane-ethyl acetate (1:3). The azadirachtin-containing fractions (70–80% pure) are combined and azadirachtin is crystallized using carbon tetrachloride. Final purification is by flash chromatography in $CHCl_3$—MeCN, 3:1.

Existing azadirachtin-containing solids, while offering advantages over liquid preparations, are unstable and have unique storage requirements. Schroeder and Nakanishi recognized the instability of their solid product, noting that the material has a half-life of about 4 months in the solid state in flasks at room temperature. Id. at 243, note 3.

It would be desirable to provide a storage-stable, azadirachtin-containing solid that could be combined with diluents, surfactants or dispersants to produce a storage-stable biocontrol agent.

SUMMARY OF THE INVENTION

The present invention is summarized in that the stability of an azadirachtin-containing solid is enhanced by the removal from the solid of volatile polar solvents to a level of about 5% by weight or less, and less than 1% water.

It is an object of the present invention to provide a solid azadirachtin formulation that is more stable than existing solid formulations, and which avoids the unique storage requirements of existing formulations.

It is an advantage of the present invention that solid azadirachtin containing about 5% or less by weight of volatile polar solvents and less than 1% water is lighter, more readily transported, and less flammable than existing liquid formulations. Moreover, the formulation of the present invention maintains its stability even over long storage periods.

Other objects, advantages, and features of the present invention will become apparent upon consideration of the following detailed description.

DETAILED DESCRIPTION OF THE INVENTION

The present invention relates to a storage-stable azadirachtin-containing solid and biocontrol formulations prepared therefrom. The biocontrol formulation can be the azadirachtin-containing solid itself obtained from neem seeds, but is preferably the solid as formulated, in a manner known to the art, in combination with diluents, surfactants or dispersants to prepare a biocontrol formulation suitable for storage, transport and use as a biocontrol agent. References herein to a "solid biocontrol formulation" includes both the azadirachtin-containing solid obtained from seeds as well as the solid in combination with diluents, surfactants or dispersants. "Biocontrol" includes insecticidal or pesticidal activity. Biocontrol also includes such insect- and pest-avoiding activities as are known and understood to result from application of azadirachtin-containing formulations. It is understood that adequate biocontrol can be achieved without causing insect death. Biocontrol can include the ability to repel insects and other pests from plant surfaces, kill pests at various life stages, in particular the egg and larval stage, and control fungal pathogens. In this application, a "storage stable" azadirachtin-containing solid retains its free-flowing appearance after 2 weeks of storage at 55° C. in a sealed container. The azadirachtin in a preferred storage-stable solid formulation also has a total azadirachtin decomposition rate constant of less than 0.03 1/day and is least 75% undegraded after 2 weeks of storage at 55° C. in a sealed container.

Although an azadirachtin-containing solid prepared according to any known method can be advantageously treated according to the method of the present invention, the azadirachtin-containing solid is preferably prepared according to the method of Roland, et al. (U.S. Pat. No. 5,397,571), which is incorporated herein by reference.

The Roland et al. process involves extracting ground neem seeds with a co-solvent mixture of a nonpolar, aliphatic hydrocarbon solvent and a polar solvent for a time period and at a temperature sufficient to obtain a neem extract having both the hydrophilic azadirachtin-containing portion and the hydrophobic neem oil portion of the seeds. The extraction process may be performed at a temperature of about 25° C. up to the boiling temperature of the co-solvent extraction. Preferably, the extraction is accomplished at a temperature of about 40° C. to about 60° C. The extraction is performed for a period of time sufficient to obtain optimum extraction of the neem seeds. Preferably, the extraction process is carried out for about 2 to about 12 hours. If desired, the co-extraction process may be repeated to optimize the extraction efficiency. Following extraction, the co-solvent neem extract is treated to separate the hydrophilic and hydrophobic portions of the extract.

The Roland et al. extraction process can be accomplished using various combinations of a nonpolar, aliphatic hydrocarbon solvent and a polar solvent. For purposes of this invention, nonpolar, aliphatic hydrocarbons include those aliphatic hydrocarbons having high neem oil solubility and substantially no azadirachtin or water solubility. Suitable aliphatic hydrocarbons include, but are not limited to, aliphatic hydrocarbons and halogenated aliphatic hydrocarbons having from 1 to 20, preferably 1 to 10 carbon atoms, e.g., pentane, hexane, heptane, octane, nonane, decane, isoctane, chloropentane, chlorohexane, and the like, and their isomers; petroleum distillates, petroleum ether, and the like, and mixtures thereof. Various other nonpolar aliphatic hydrocarbons having the above characteristics are well known to those skilled in the art, and the choice of a particular solvent is not per se critical provided that it is substantially azadirachtin-insoluble and neem oil has a high degree of solubility therein. Preferably, the nonpolar aliphatic hydrocarbon solvent is miscible with the polar solvent of choice to form a substantially homogenous solution.

Polar solvents useful in the co-extract process include any polar solvent which has a high degree of azadirachtin solubility. Preferably, the polar solvent is miscible with the nonpolar solvent to form a substantially homogenous solution. Suitable polar solvents include, but are not limited to, aliphatic alcohols, ketones, nitriles, substituted aromatics, such as alkylated or halogenated aromatics, amide sulfoxides, alkyl carbonates, chlorinated aliphatics, aromatic aldehydes, sulfones, ethers, esters, and the like, or mixtures thereof. Preferred polar solvents for use in the co-extraction method include, but are not limited to, aliphatic alcohols such as methanol, ethanol, propanol, isopropanol, butanol, 2-butanol, t-butanol, benzyl alcohol, and the like, and mixtures thereof. The term alkyl as used herein refers to alkyl groups having from 1–10, preferably 1 to 6 carbon atoms.

The concentration of nonpolar aliphatic hydrocarbon solvent and polar solvents useful in the co-extraction process will vary. In general, the nonpolar, aliphatic hydrocarbon and polar solvents should be present in the solvent mixture in an amount sufficient to permit extraction of both the hydrophilic and hydrophobic components desired from the neem seeds. Suitable solvent mixtures useful in the present invention may include about 10 to about 90 weight percent of the nonpolar, aliphatic hydrocarbon solvent and about 90 to about 10 weight percent of the polar solvent. Preferably, the solvent mixtures useful in the invention include about 40 to about 70 weight percent of the nonpolar, aliphatic hydrocarbon solvent and about 30 to about 60 weight percent of the polar solvent; most preferably about 60 weight percent of the nonpolar, aliphatic hydrocarbon solvent and about 40 weight percent of the polar solvent.

Separation of the hydrophilic and hydrophobic portions of the solvent extract mixture is carried out by means known to one skilled in the art. In a preferred embodiment, a counter-extraction process is used. In the counter-extraction process, the co-solvent neem extract is stripped of solvent to recover "neem extract mixture." The term "neem extract mixture" is used to designate a neem extract containing both the hydrophilic, azadirachtin-containing portion of the neem seeds and the hydrophobic neem oil portion of the seeds from which substantially all of the extraction co-solvent has bene removed. The neem extract mixture is thereafter contacted with a solvent having a sufficiently low polarity, i.e., hexane, to precipitate as a solid the hydrophilic, azadirachtin-containing portion of the extract. The solid is recovered by known techniques, e.g., filtration. The azadirachtin-containing solid formed by this method contains high concentrations of azadirachtin, i.e., greater than 10 weight percent, preferably greater than 15 weight percent, most preferable greater than 20 weight percent, of azadirachtin. The remaining hydrophobic neem oil portion of the extract mixture is recovered from the filtrate by removing the solvent.

The azadirachtin-containing solid appears to be a dry, white-to-beige, free-flowing powder. The solid can be combined, in a manner known to the art, with such diluents, surfactants or dispersants to form various formulations suitable for application as an insecticide or pesticide. The formulations thus prepared are advantageous over emulsifiable liquid formulations because they are lighter, and therefore, more readily transported. Also, untreated azadirachtin-containing solids are subject to considerable rapid degradation under standard storage conditions, and thus, to decreased activity of formulations incorporating the solid. As the Examples set forth below demonstrate, the presence in the azadirachtin-containing solid of volatile polar compounds contribute directly to decreased stability of the solid. In contrast, the materials treated according to the method of the present invention are storage-stable. Accordingly, while it is greatly preferred to be able to commercially transport solid material rather than liquid material, there has heretofore been no practical way to prepare an azadirachtin-containing solid that retains sufficient biocontrol activity during necessary shipping and storage times.

In accordance with the formulations prepared according to the present invention, volatile polar solvents are removed in the azadirachtin-containing solid, and are preferably reduced to a level at or below about 5%, by drying the azadirachtin. By "about 5%," the applicants intend to include solid formulations having a total concentration of volatile polar solvents close to 5% that also exhibit the characteristic ability to remain as a white-to-beige, free-flowing solid after storage at 55° C. for two weeks. The concentration of volatile polar solvents is preferably lower than 2% and is most preferably 1% or less, by weight of the solid. Likewise, the concentration of volatile polar solvents can be as low as zero, if all are removed during the drying step. "Polar solvents" include water and any other polar solvent useful in preparing the azadirachtin-containing solid, including, but not limited to, those noted above in connection with the preparation of the solid material according to the method of Roland et al., as incorporated herein by reference. "Alcohol" is intended to encompass any alcohol that can, by virtue of its polar nature, be used in the preparation of azadirachtin from neem plant material. It is understood in the art that the polarity of particular aliphatic alcohols (methanol, ethanol, propanol, butanol, etc.) or branched alcohols affects the recovery of azadirachtin from neem, and that although ethanol is widely used in azadirachtin purification, other alcohols could be used which might then contaminate the solid azadirachtin preparation and which would be advantageously removed in the present method.

Drying is preferably accomplished by heating in an oven at a temperature and for a time sufficient to reduce the content of the volatile solvents to less than about 5% (preferably to less than 1%), and water to less than 1%. The samples are placed in unsealed containers during the drying step, to allow the volatile polar solvents to escape from the solid azadirachtin. The temperature selected for atmospheric drying should be uniform and is preferably higher than room temperature but below the melting point of the solid azadirachtin-containing formulation. In the alternative, a drying temperature below room temperature can be selected. A sufficient drying time can be determined empirically by routine testing of the solid during drying to determine whether the solid contains less than about 1% by weight of volatile polar solvents.

Those of ordinary skill in the art will also appreciate that other drying methods could be applied to solid azadirachtin-containing preparations to make the storage-stable preparation of the present invention. Such methods would include lyophilizing or exposing the solid preparation to a desiccant. The method by which volatile polar solvents are removed from the azadirachtin-containing solid are not intended to be a limitation upon the scope of this invention.

The storage stability of an azadirachtin-containing solid comprising less than about 1% water and 5% volatile polar solvents, and the degradative effect of polar solvents on stability, are demonstrated in the following examples, which are intended to be merely exemplary of the invention and not limiting thereof.

EXAMPLES

1. Solid azadirachtin containing more than about 1% water decomposes during storage at 55° C. for a matter of weeks A number of samples of azadirachtin-containing white-to-beige solid from five different lots, prepared according to the method of Roland et al. (U.S. Pat. No. 5,397,571, incorporated herein by reference) were placed into separate 1-dram capped glass vials and stored in an oven at 55° C. Over the next several weeks, small solid samples from each lot were removed from the oven and were analyzed for appearance and azadirachtin content. The results, shown in Table 1, revealed that samples from lots 002, 003, and 004 evidenced significant azadirachtin decomposition coupled with a brown, melted appearance. In contrast, the samples of 006 and 009 remained white and evidenced very little azadirachtin decomposition and retained their characteristic free-flowing property. These attributes are characteristic both of azadirachtin-containing solids prepared and treated as described, and of the such solids provided in a formulation with appropriate surfactants or diluents. The ability to retain the free-flowing property, even in a formulation, depends upon the removal from the reduction of solvents in the solids to an acceptable level.

Further analysis of the samples, performed after 14 days at 55° C. suggested that the presence of water had a marked negative impact on azadirachtin stability. It was observed that, while each of the solid samples differed little in sulfur content, the water content of brown samples 002, 003, and 004 was greater than 1%, while white samples 006 and 009 had less than 1% water.

Three values are given in the tables for each azadirachtin level: The amount (in grams) of azadirachtin A is given before the slash. The amount of azadirachtin B (in grams) is given after the slash. The total azadirachtin amount is given in parentheses. $K_a$, $K_b$, and $K_t$ refer to the first order decomposition rate constants (with units of 1/day) for azadirachtin A, azadirachtin B, and total azadirachtin, respectively.

TABLE 1

| Days at Temperature | 002 | 003 | 004 | 006 | 009 |
| --- | --- | --- | --- | --- | --- |
| 0 | 18.5/6.15 (24.6) | 17.6/4.50 (22.1) | 17.5/4.65 (22.2) | 17.9/4.93 (22.8) | 17.5/5.76 (23.3) |
| 2 | 16.9/5.5 (22.5) | 16.2/4.19 (20.4) | 12.5/4.05 (16.6) | 17.7/4.76 (22.7) | 17.2/5.60 (23.8) |
| 7 | 10.5/3.4 (13.9) | 15.4/4.26 (19.7) | 7.42/2.97 (10.4) | 17.9/5.26 (23.2) | 17.0/5.79 (22.8) |
| 14 | 9.1/3.1 (12.2) | 9.31/3.15 (12.4) | 6.1/2.2 (8.3) | 15.4/4.66 (20.1) | 16.3/5.63 (21.9) |
| 30 | 9.12/3.1 (12.2) | 9.64/3.23 (12.9) | | | |
| Decomposition Rate Constants | | | | | |
| Ka (1/day) [Azad A] | 0.05 | 0.041 | 0.078 | 0.007 | 0.006 |
| Kb (1/day) [Azad B] | 0.05 | 0.036 | 0.053 | 0.005 | <0.005 |
| Kt (1/day) [Azad Total] | 0.05 | 0.04 | 0.07 | 0.007 | 0.004 |
| Physical State at End of Testing | Brown melted | Brown Granular | Brown Melted | White | White |
| % $H_2O$ | 5.23 | 2.66 | 1.73 | 0.75 | 0.82 |
| Sulphur | 0.72 | 0.66 | 0.68 | 0.59 | — |

2. An increase in water concentration converts a stable azadirachtin formulation to an unstable formulation A sample of azadirachtin from lot 009, shown to be stable at 55° C. in Example 1, was mixed with $H_2O$ (13%) to homogeneity and then placed in a sealed glass vial into an oven at 55° C. After 1 week, the sample had turned brown and melted. Subsequent chemical analysis (according to the HPLC protocol of Hull, et al., *J. Chromatography* 633:300–304(1993)) revealed substantial azadirachtin decomposition. This sample is identified as 009WW in Table 2. Table 2 confirms that the stability of solid azadirachtin is directly affected by the presence in the solid of water and suggests that removal of water from the solid increases the shelf life of solid azadirachtin.

TABLE 2

| Days at Temperature | 009 | 009WW |
| --- | --- | --- |
| 0 | 17.5/5.76 (23.3) | 18.4/6.22 (24.6) |
| 2 | 17.2/5.60 (23.8) | — |
| 7 | 17.0/5.79 (22.8) | 14.1/5.26 (19.4) |
| 14 | 16.3/5.63 (21.9) | 6.75/3.11 (9.86) |
| 30 | 9.64/3.23 (12.9) | |
| Decomposition Rate Constants | | |
| Ka (1/day) [Azad A] | 0.006 | 0.07 |
| Kb (1/day) [Azad B] | <0.005 | 0.05 |

TABLE 2-continued

| Kt (1/day) [Azad Total] | 0.004 | 0.07 |
| --- | --- | --- |
| Physical State at End of Testing | White | Brown Melted |
| % $H_2O$ | 0.82 | 13 |

3. Dry solid azadirachtin has a longer shelf life than azadirachtin containing water or ethanol Dry solid azadirachtin was obtained by drying a solid azadirachtin sample from Lot 14 (014) in an oven at 55° C. for 24 hours in an unsealed vessel until the volatile content of the solid was less than 0.5%. The dried sample was then split into 6 subsamples. One dry subsample (014D) was used without further treatment. A second subsample (014W1) received 1% by weight of $H_2O$. A third subsample (014W4) received 4% by weight $H_2O$. Subsamples 4, 5 and 6 received 1, 3, and 5% by weight of ethanol, respectively and were designated 014E1, 014E3, and 014E5. The subsamples were placed in multiple tightly sealed vials at 55° C. Individual vials were removed periodically to assay for azadirachtin. The results presented in Table 3 show that the dried sample, or samples containing 1% by weight $H_2O$ or ethanol are much more stable than the samples containing higher amounts of the polar solvent. It was also observed, from the results of Table 3, that higher levels of ethanol have somewhat less of an effect on stability than comparable levels of water in the solid.

TABLE 3

| Initial Composition | 014 | 014D | 014W1 | 014W4 | 014E1 | 014E3 | 014E5 |
| --- | --- | --- | --- | --- | --- | --- | --- |
| % Volatile | 2.4 | <.5 | 1.1% | 4.1% | 1.1% | 3.1% | 5.1% |
| % $H_2O$ | 1.2 | <.5 | 1% | 4.0 | 0.1 | 0.1 | 0.1 |
| % EtOH | 1.2 | <.5 | <.5 | <.5% | 1.0% | 3% | 5% |

TABLE 3-continued

| Days Storage | Stability at 55° C. | | | | | | |
|---|---|---|---|---|---|---|---|
| 0 | 10.9/4.1 (15.0) | 10.9/4.2 (15.1) | 10.9/4.4 (15.2) | 10.9/4.4 (15.0) | 10.8/4.3 (15.2) | (10.1)/4.4 (15.1) | 10.8/4.0 (19.8) |
| 7 | — | — | 7.9/3.4 (11.3) | 5.9/2.7 (8.6) | — | — | — |
| 14 | 7.0/3.0 (10.0) | 9.88/3.65 (13.5) | 7.6/3.3 (10.9) | 3.5/21 (5.6) | 6.6/3.0 (9.7) | 6.1/2.9 (9.0) | 4.3/2.4 (6.7) |
| 30 | 3.9/2.57 6.4 | 10.3/4.3 (14.4) | — | — | — | — | — |
| Ka (1/day) | .034 | .007 | .026 | .08 | .035 | .040 | .065 |
| Kb (1/day) | .015 | — | .02 | .057 | .026 | .030 | .037 |
| Kt (1/day) | .029 | .007 | .024 | .07 | .03 | .04 | .057 |

Thus it has been demonstrated that azadirachtin-containing solids can be storage stabilized by drying at a temperature and for a time sufficient to reduce the volatile concentration of polar solvents to 1.5% or lower, preferably to 1.0% or lower, and most preferably to 0.5% or lower. Heating at 55° C. for a short period of time such as 24 hours seems to have little or no effect upon azadirachtin stability. The preferred heating time can be determined empirically and is a function of the amount of polar solvent trapped within the solid. For example, as is shown in Table 3, less decomposition is observed after treating a dried sample for 30 days than is observed after treating a sample containing 1% water for only 7 days. Similarly, decomposition is greater after 7 days in a sample containing 4% water than a sample containing 1% water.

The preceding examples are intended only as exemplary, but not limiting, of the present invention, which is intended to encompass all such variations and modifications as come within the scope of the following claims.

We claim:

1. A solid biocontrol formulation comprising azadirachtin; one or more volatile polar solvents at a total concentration of no more than about five weight percent; and water at no more than 1%, wherein the biocontrol formulation is free-flowing after storage in a sealed container at 55° C. for two weeks.

2. A solid biocontrol formulation claimed in claim 1 wherein one of the volatile polar solvents is selected from the group consisting of an aliphatic alcohol, a ketone, a nitrile, a substituted aromatic, an amide sulfoxide, an alkyl carbonate, a chlorinated aliphatic, an aromatic aldehyde, a sulfone, an ether, an ester, mixtures thereof and water.

3. A solid biocontrol formulation as claimed in claim 2 wherein the aliphatic alcohol is ethanol.

4. A solid biocontrol formulation as claimed in claim 1 wherein the total concentration of the volatile polar solvents is below about 1 weight percent.

5. A solid biocontrol formulation as claimed in claim 1 wherein the total concentration of the volatile polar solvents is below 0.5 weight percent.

6. A solid biocontrol formulation as claimed in claim 1 wherein the azadirachtin has a total decomposition rate constant of 0.03 per day or less and is least 75% undegraded after 2 weeks of storage at 55° C. in a sealed container.

7. A solid biocontrol formulation as claimed in claim 1 further comprising a solid diluent present in the formulation at an amount of up to 99 percent by weight.

8. A solid biocontrol formulation as claimed in claim 1 further comprising a surfactant present in the formulation at an amount of five percent or less by weight.

9. A solid biocontrol formulation as claimed in claim 8 wherein the surfactant is present in the formulation at an amount of between 0.05 percent and 2 percent by weight.

10. A method for forming a solid biocontrol formulation, the method comprising the steps of:
    reducing the volatile polar solvents in an azadirachtin-containing solid to about 5% by weight or less; and
    reducing the water in the azadirachtin-containing solid to about 1% or less.

11. A method as claimed in claim 10, the method comprising the step of:
    reducing the volatile polar solvents in an azadirachtin-containing solid to about 1% by weight or less.

* * * * *